(12) United States Patent
Yiannikouros et al.

(10) Patent No.: US 8,258,334 B2
(45) Date of Patent: Sep. 4, 2012

(54) N-ALKANOYL-N,N',N'-ALKYLENEDIAMINE TRIALKANOIC ACID ESTERS

(75) Inventors: George Petros Yiannikouros, Florence, SC (US); Panos Kalaritis, Florence, SC (US)

(73) Assignee: Irix Pharmaceuticals, Inc., Florence, SC (US)

( * ) Notice: Subject to any disclaimer, the term of this patent is extended or adjusted under 35 U.S.C. 154(b) by 433 days.

(21) Appl. No.: 12/617,436

(22) Filed: Nov. 12, 2009

(65) Prior Publication Data
US 2010/0130770 A1     May 27, 2010

Related U.S. Application Data

(60) Provisional application No. 61/113,884, filed on Nov. 12, 2008.

(51) Int. Cl.
C07C 229/24      (2006.01)
(52) U.S. Cl. ..................................................... 560/169
(58) Field of Classification Search .................. None
See application file for complete search history.

(56) References Cited

U.S. PATENT DOCUMENTS

| | | | |
|---|---|---|---|
| 4,142,061 A | 2/1979 | Wilkes | |
| 4,144,182 A | 3/1979 | Bereuter | |
| 4,269,730 A | 5/1981 | Wechsler et al. | |
| 4,954,142 A | 9/1990 | Carr et al. | |
| 5,177,243 A | 1/1993 | Parker | |
| 5,191,081 A | 3/1993 | Parker | |
| 5,191,106 A | 3/1993 | Parker | |
| 5,250,728 A | 10/1993 | Parker et al. | |
| 5,284,972 A * | 2/1994 | Parker et al. | 562/565 |
| 5,449,822 A | 9/1995 | Parker et al. | |
| 5,621,008 A | 4/1997 | Ptchelintsev | |
| 5,643,864 A | 7/1997 | Li et al. | |
| 5,744,063 A | 4/1998 | Desai et al. | |
| 5,821,215 A | 10/1998 | Crudden et al. | |
| 5,869,441 A | 2/1999 | Fair et al. | |
| 5,886,031 A | 3/1999 | Wilkes | |
| 5,914,310 A | 6/1999 | Li et al. | |
| 5,952,291 A | 9/1999 | Desai et al. | |
| 6,503,873 B1 | 1/2003 | Crudden et al. | |
| 2003/0054021 A1 | 3/2003 | Dalko et al. | |
| 2005/0255172 A1 | 11/2005 | Omidbakhsh | |
| 2007/0131623 A1 | 6/2007 | Javora et al. | |
| 2008/0318824 A1 | 12/2008 | Iwai et al. | |

FOREIGN PATENT DOCUMENTS

| | | |
|---|---|---|
| CA | 2085155 | 6/1993 |
| EP | 0 740 015 | 10/1996 |
| EP | 0 834 307 | 4/1998 |
| EP | 0 629 608 | 10/1998 |
| JP | 09-235592 | 9/1997 |
| JP | 11035537 A * | 2/1999 |
| WO | WO 2010/056854 | 5/2010 |

OTHER PUBLICATIONS

Genik-Sas-Berezow et al., "Chelating Polymers I. The synthesis and acid dissociation behavior of several N-(p vinylbenzenesulfonyl)-substituted diaminopolyacetic acid monomers, monomeric analogs, and related intermediates," Canadian Journal of Chemistry. vol. 48 pp. 163-175 (1970).
Notification of Transmittal of the International Search Report and the Written Opinion of the International Searching Authority, or the Declaration corresponding to International Patent Application No. PCT/US2009/064195 dated Feb. 1, 2010.
Notification Concerning Transmittal of International Preliminary Report on Patentability (Chapter I of the Patent Cooperation Treaty) corresponding to International Patent Application No. PCT/US2009/064195 dated May 26, 2011.

* cited by examiner

*Primary Examiner* — Paul A Zucker
(74) *Attorney, Agent, or Firm* — Jenkins, Wilson, Taylor & Hunt, P.A.

(57) ABSTRACT

A method of preparing a N-acyl-N,N',N'-alkylenediamine trialkanoic acid ester comprising contacting a cyclic amidine with an ester of a haloalkanoic acid is provided. In some embodiments, the method involves preparing a N-acyl-N,N', N'-ethylenediamine trialkanoic acid ester by contacting a 2-alkyl imidazoline with the ester of haloalkanoic acid. In some embodiments, the N-acyl-N,N',N'-alkylenediamine trialkanoic acid ester is a synthetic intermediate in the preparation of a N-acyl-N,N',N'-alkylenediamine trialkanoic acid or a salt thereof. In some embodiments, the method provides novel N-acyl-N,N',N'-alkylenediamine trialkanoic acids and/ or esters, which can be used, for example, as chelating agents.

29 Claims, No Drawings

N-ALKANOYL-N,N',N'-ALKYLENEDIAMINE TRIALKANOIC ACID ESTERS

CROSS REFERENCE TO RELATED APPLICATIONS

This application claims the benefit of U.S. Provisional Patent Application Ser. No. 61/113,884, filed Nov. 12, 2008, the disclosure of which is incorporated herein by reference in its entirety.

TECHNICAL FIELD

The presently disclosed subject matter relates to N-acyl-N,N',N'-alkylenediamine trialkanoic acid esters, such as N-acyl-N,N',N'-ethylenediamine trialkanoic acid esters; their synthesis; and their use as chelating agents and as intermediates in the synthesis of N-acyl-N,N',N'-alkylenediamine trialkanoic acids and their salts.

BACKGROUND

Surfactants are materials which can be generally described as having at least one hydrophobic moiety and at least one hydrophilic moiety per molecule. Surfactants can be classified as anionic, cationic, nonionic, and amphoteric. For example, anionic surfactants can be molecules that can have a negative charge on a hydrophilic moiety, such as in the form of a carboxylate, phosphate, sulfate, or sulfonate. Surfactants can have numerous uses, including as emulsifiers, detergents, dispersants and solubilizing agents. They can find use in emulsion polymerization, as well as in agricultural chemicals, personal care and household products, industrial and institutional cleaners, textile treatments, in oil recovery agents, and in corrosion inhibitors. Thus, they can function as cleaners, wetting agents, and foaming and frothing agents (e.g., for shampoos, car washes, carpet cleaners, dishwashing detergents and the like).

Accordingly, there is an ongoing need for methods of synthesizing surfactants, such as facile methods that provide high yields, as well as synthetic routes that can provide various surfactants and chelating agents.

SUMMARY

In some embodiments, the presently disclosed subject matter provides a method of preparing a compound of Formula (I):

wherein:
$Z_1$ can be present or absent and when present is $—[C(R_4)_2]_m—$;
m is an integer from 1 to 4;
each X is $—CHR_5—[C(R_6)_2]_n—$;
each n is independently an integer from 0 to 4;
$R_1$ is selected from the group consisting of H, alkyl, cycloalkyl, substituted alkyl, aralkyl, aryl, and substituted aryl;

each $R_2$ is independently selected from the group consisting of alkyl, cycloalkyl, substituted alkyl, aralkyl, aryl, and substituted aryl;
each $R_3$ and each $R_4$ independently selected from the group consisting of H, alkyl, cycloalkyl, substituted alkyl, aralkyl, aryl, and substituted aryl, or wherein one $R_3$ and one $R_4$ are together alkylene, substituted alkylene, aralkylene, or substituted aralkylene, or wherein two $R_4$ are together alkylene, substituted alkylene, aralkylene, or substituted aralkylene;
each $R_5$ is selected from the group consisting of H, alkyl, cycloalkyl, substituted alkyl, aralkyl, aryl, and substituted aryl; and
each $R_6$ is independently selected from the group consisting of H, alkyl, alkoxy, cycloalkyl, aralkyl, aralkoxy, aryloxy, aryl, and substituted aryl;
wherein the method comprises: providing a cyclic amidine compound, wherein the cyclic amidine compound is a cyclic amidine wherein the amidine nitrogen atoms are linked via an alkylene or aralkylene group; and contacting the cyclic amidine compound with an ester of a haloalkanoic acid in the presence of a base.

In some embodiments, $R_1$ is selected from the group consisting of alkyl, cycloalkyl, substituted alkyl, aralkyl, aryl, and substituted aryl, and the cyclic amidine is a compound of Formula (II):

wherein:
$Z_2$ can be present or absent and when present is $—[C(R_9)_2]_m—$;
m is an integer from 1 to 4;
$R_7$ is selected from the group consisting of alkyl, cycloalkyl, substituted alkyl, aralkyl, aryl and substituted aryl; and
each $R_8$ and each $R_9$ are independently selected from the group consisting of H, alkyl, cycloalkyl, substituted alkyl, aralkyl, aryl and substituted aryl, or wherein one $R_8$ and one $R_9$ together are alkylene, substituted alkylene, aralkylene, or substituted aralkylene, or wherein two $R_9$ together are alkylene, substituted alkylene, aralkylene, or substituted aralkylene.

In some embodiments, the cyclic amidine is a 2-substituted imidazoline. In some embodiments, the compound of Formula (I) has a structure of Formula (Ia):

wherein:
each X is $—CHR_5—[C(R_6)_2]_n—$;
each n is independently an integer from 0 to 4;
$R_1$ is selected from the group consisting of alkyl, cycloalkyl, substituted alkyl, aralkyl, aryl, and substituted aryl;

each $R_2$ is independently selected from the group consisting of alkyl, cycloalkyl, substituted alkyl, aralkyl, aryl, and substituted aryl;

$R_3$ and $R_4$ are independently selected from the group consisting of H, alkyl, cycloalkyl, substituted alkyl, aralkyl, aryl, and substituted aryl, or wherein $R_3$ and $R_4$ together are alkylene, substituted alkylene, aralkylene, or substituted aralkylene;

each $R_5$ is selected from the group consisting of H, alkyl, cycloalkyl, substituted alkyl, aralkyl, aryl, and substituted aryl; and each $R_6$ is independently selected from the group consisting of H, alkyl, alkoxy, cycloalkyl, aralkyl, aralkoxy, aryloxy, aryl, and substituted aryl.

In some embodiments, each n is 0. In some embodiments, $R_1$ is alkyl. In some embodiments, the alkyl is straight-chain, saturated alkyl. In some embodiments, alkyl is C1-C12 alkyl. In some embodiments, alkyl is C8 alkyl.

In some embodiments, $R_1$ has a structure of one of the formulas:

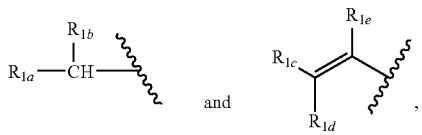

wherein $R_{1a}$ and $R_{1b}$ are independently selected from the group consisting of alkyl, substituted alkyl, cycloalkyl, aralkyl, aryl, and substituted alkyl, and wherein $R_{1c}$, $R_{1d}$ and $R_{1e}$ are independently selected from the group consisting of H, alkyl, substituted alkyl, cycloalkyl, aralkyl, aryl, and substituted alkyl.

In some embodiments, each $R_2$ is C1-C6 alkyl. In some embodiments, each $R_2$ is ethyl. In some embodiments, $R_3$ and $R_4$ are independently selected from H and alkyl. In some embodiments, each $R_5$ is selected from the group consisting of H and alkyl.

In some embodiments, the 2-substituted imidazoline is a compound of Formula (IIa):

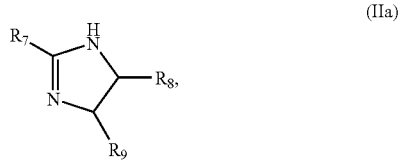

(IIa)

wherein:

$R_7$ is selected from the group consisting of alkyl, cycloalkyl, substituted alkyl, aralkyl, aryl and substituted aryl; and $R_8$ and $R_9$ are independently selected from the group consisting of H, alkyl, cycloalkyl, substituted alkyl, aralkyl, aryl and substituted aryl, or wherein $R_8$ and $R_9$ together are alkylene, substituted alkylene, aralkylene, or substituted aralkylene.

In some embodiments, $R_7$ is saturated alkyl. In some embodiments, $R_7$ is C1-C12 alkyl. In some embodiments, one or both of $R_8$ and $R_9$ is H. In some embodiments, one or both of $R_8$ and $R_9$ is alkyl. In some embodiments, one or both of $R_8$ and $R_9$ is methyl.

In some embodiments, the ester is the ester of an α-haloacetic acid or a mixture thereof. In some embodiments, the ester is ethyl chloroacetate, ethyl bromoacetate, or a mixture thereof.

In some embodiments, the contacting is performed in an aprotic, non-polar solvent. In some embodiments, the aprotic, non-polar solvent is toluene. In some embodiments, the base is sodium bicarbonate.

In some embodiments, the presently disclosed subject matter provides a method for preparing a N-acyl-N,N',N'-alkylenediamine trialkanoic acid or a salt thereof, wherein the method comprises: providing a cyclic amidine compound, wherein the cyclic amidine compound is a cyclic amidine wherein the amidine nitrogen atoms are linked via an alkylene or aralkylene group; contacting the cyclic amidine compound with an ester of a haloalkanoic acid in the presence of a first base to provide a compound of Formula (I); and contacting the compound of Formula (I) with a second base.

In some embodiments, the N-acyl-N,N',N'-alkylenediamine trialkanoic acid or salt thereof is a N-acyl-N,N',N'-ethylenediamine-trialkanoic acid or a salt thereof, and providing the cyclic amidine compound comprises providing a 2-substituted imidazoline, contacting the cyclic amidine compound with the ester of a haloalkanoic acid in the presence of the first base to provide the compound of Formula (I) comprises contacting the 2-substituted imidazoline with the ester of a haloalkanoic acid in the presence of the first base to provide a compound of Formula (I) wherein the compound of Formula (I) is a compound of Formula (Ia); and contacting the compound of Formula (I) with the second base comprises contacting the compound of Formula (Ia) with the second base.

In some embodiments, the second base is an alkali metal hydroxide. In some embodiments, contacting the compound of Formula (I) with the second base comprises providing a mixture comprising the compound of Formula (I) and the second base; mixing the mixture for a period of time; and acidifying the mixture with an acid.

In some embodiments, the presently disclosed subject matter provides a compound of Formula (I), subject to the proviso that when $Z_1$ is present and m is 1, at least one $R_3$ or one $R_4$ is not H. In some embodiments, the compound of Formula (I) is a compound of Formula (Ia). In some embodiments, the compound is selected from:

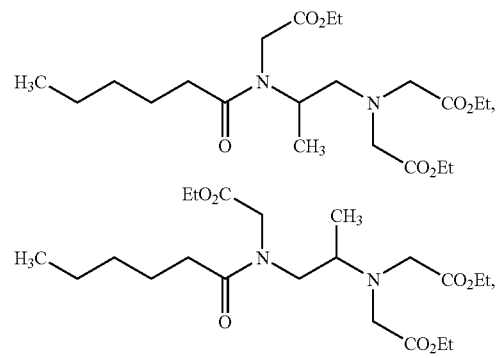

and mixtures thereof. In some embodiments, the presently disclosed subject matter provides a composition comprising a compound of Formula (I).

In some embodiments, the presently disclosed subject matter provides a compound of Formula (III):

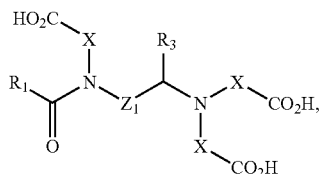

wherein:
$Z_1$ can be present or absent and when present is —[C$(R_4)_2]_m$—;
m is an integer from 1 to 4;
each X is —CHR$_5$—[C$(R_6)_2]_n$—;
each n is independently an integer from 0 to 4;
$R_1$ is selected from the group consisting of H, alkyl, cycloalkyl, substituted alkyl, aralkyl, aryl, and substituted aryl;
each $R_2$ is independently selected from the group consisting of alkyl, cycloalkyl, substituted alkyl, aralkyl, aryl, and substituted aryl;
each $R_3$ and each $R_4$ are independently selected from the group consisting of H, alkyl, cycloalkyl, substituted alkyl, aralkyl, aryl, and substituted aryl, or wherein one $R_3$ and one $R_4$ are together alkylene, substituted alkylene, aralkylene, or substituted aralkylene, or wherein two $R_4$ are together alkylene, substituted alkylene, aralkylene, or substituted aralkylene;
each $R_5$ is selected from the group consisting of H, alkyl, cycloalkyl, substituted alkyl, aralkyl, aryl, and substituted aryl; and
each $R_6$ is independently selected from the group consisting of H, alkyl, alkoxy, cycloalkyl, aralkyl, aralkoxy, aryloxy, aryl, and substituted aryl; or a salt thereof, and subject to the proviso that when $Z_1$ is present and m is 1, at least one $R_3$ or one $R_4$ is not H.

In some embodiments, $Z_1$ is present and m is 1 and the compound of Formula (III) is a compound of Formula (IIIa):

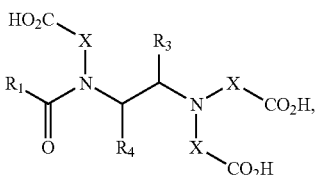

wherein:
each X is —CHR$_5$—[C$(R_6)_2]_n$—;
each n is independently an integer from 0 to 4;
$R_1$ is selected from the group consisting of alkyl, cycloalkyl, substituted alkyl, aralkyl, aryl, and substituted aryl;
each $R_2$ is independently selected from the group consisting of alkyl, cycloalkyl, substituted alkyl, aralkyl, aryl, and substituted aryl;
$R_3$ and $R_4$ are independently selected from the group consisting of H, alkyl, cycloalkyl, substituted alkyl, aralkyl, aryl, and substituted aryl, or wherein $R_3$ and $R_4$ together are alkylene, substituted alkylene, aralkylene, or substituted aralkylene; subject to the proviso that one or both of $R_3$ and $R_4$ are not H;

each $R_5$ is independently selected from the group consisting of H, alkyl, cycloalkyl, substituted alkyl, aralkyl, aryl, and substituted aryl; and
each $R_6$ is independently selected from the group consisting of H, alkyl, alkoxy, cycloalkyl, aralkyl, aralkoxy, aryloxy, aryl, and substituted aryl; or a salt thereof.

In some embodiments, the presently disclosed subject matter provides a composition comprising a compound of Formula (III) or a salt thereof.

Accordingly, it is an object of the presently disclosed subject matter to provide a method of preparing compounds of Formula (I) and Formula (III), including, for example, N-acyl-N,N',N'-ethylenediamine trialkanoic acids and esters, as well as to provide the compounds themselves.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. DEFINITIONS

Following long-standing patent law convention, the terms "a", "an", and "the" refer to "one or more" when used in this application, including the claims. Thus, for example, reference to "a solvent" includes mixtures of one or more solvents, two or more solvents, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, molar equivalents, time, temperature, etc. is meant to encompass in one example variations of ±20% or ±10%, in another example ±5%, in another example ±1%, and in yet another example ±0.1% from the specified amount, as such variations are appropriate to perform the disclosed methods.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-11}$ straight-chain alkyls. In other embodiments, "alkyl" refers, in particular, to $C_{1-6}$ straight-chain alkyls.

Alkyl groups can optionally be substituted (a "substituted alkyl") with one or more alkyl group substituents, which can be the same or different. The term "alkyl group substituent" includes but is not limited to alkyl, substituted alkyl, cycloalkyl, halo, hydroxyl, alkoxyl, aryloxyl, and aralkoxyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others.

The aryl group can be optionally substituted (a "substituted aryl") with one or more aryl group substituents, which can be the same or different, wherein "aryl group substituent" includes alkyl, substituted alkyl, cylcoalkyl, aryl, substituted aryl, aralkyl, halo, hydroxyl, alkoxyl, aryloxyl, and aralkyloxyl.

As used herein, the term "acyl" refers to a carboxylic acid group wherein the —OH of the carboxyl group has been replaced with another substituent. Thus, an acyl group can be represented by the formula RC(=O)—, wherein R is H or an alkyl, substituted alkyl, aralkyl, aryl or substituted aryl group as defined herein. As such, the term "acyl" specifically includes arylacyl groups, such as a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" and "alkoxy" refer to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" and "aryloxy" refer to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to a group comprising a mixture of aryl and alkyl groups. In some embodiments, the term "aralkyl" refers to an aryl-alkyl- group wherein aryl and alkyl are as previously described, and including substituted aryl and substituted alkyl. Exemplary aralkyl groups include benzyl, phenylethyl, and naphthylmethyl.

"Aralkyloxyl" and "aralkoxy" refer to an aralkyl-O— group wherein the aralkyl group is as previously described. An exemplary aralkyloxyl group is benzyloxyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." Thus, in some embodiments, the alkylene is a "substituted alkylene." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); butylene (—$(CH_2)_4$—); pentylene (—$(CH_2)_5$—); cyclohexylene (—$C_6H_{10}$—); cylcohexylenedimethylene (—$CH_2$—$C_6H_{10}$—$CH_2$—), —$CH_2$—CH=CH—$CH_2$—; —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—) and the like. An alkylene group can have about 2 to about 3 carbon atoms and can further have 6-20 carbons.

The term "aralkylene" refers to a bivalent aralkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. Aralkylene groups can be, for example, -alkyl-aryl- groups, -aryl-alkyl-aryl- groups, or -alkyl-aryl-alkyl- groups. The aralkylene group can optionally be substituted with one or more aryl or alkyl group substitutents. Thus, the aralkylene group can be a "substituted aralkylene." The aralkylene group can include one or more heteroatoms, such as, but not limited to N, S, O, Se, and the like, inserted in the backbone of the aryl and/or alkyl groups. Exemplary aralkylene groups include the bivalent groups formed from para, meta or ortho xylene (dimethylbenzene), i.e.:

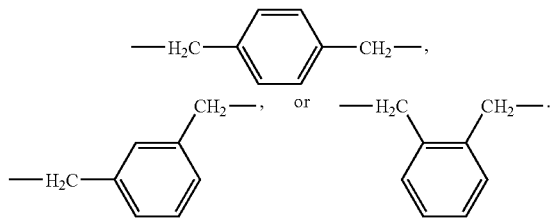

Thus, in some embodiments, the aralkylene group is selected from the group including, but not limited to, xylenylene (also referred to as phenylenedimethylene), phenylenediethylene, napthylenedimethylene, and napthylenediethylene.

The term "carboxyl" refers to the COOH group.

The terms "halo", "halide", or "halogen" as used herein refer to fluoro, chloro, bromo, and iodo groups.

"Et" refers to ethyl (i.e., —CH$_2$CH$_3$).

The term "amidine" refers to compounds that include a —C(=N)NH$_2$ or —C(=N)NHR group. As used herein, the term "cyclic amidine" refers to a compound wherein the two nitrogen atoms of an amidine group are linked by an alkylene or aralkylene linker group. Thus, for example, a cyclic amidine group can have the structure:

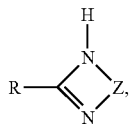

wherein Z is alkylene, substituted alkylene, aralkylene, or substituted aralkylene, and wherein R is, for example, H, alkyl, substituted alkyl, cycloalkyl, aralkyl, aryl, or substituted aryl.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" refers to a solvent molecule which can neither accept nor donate a proton. Certain aprotic solvents are non-polar solvents. Examples of nonpolar, aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. In some embodiments, the nonpolar, aprotic solvent is a solvent that has a dielectric constant that is 15 or less.

II. METHODS OF PREPARING COMPOUNDS OF FORMULA (I) AND RELATED COMPOUNDS

Hydrobically modified ethylenediamine triacetic acids have been previously described as chelating surfactants with useful properties. For instance, some N-acyl-N,N',N'-ethylenediamine triacetic acids have been described as being very mild to the skin (see, e.g., U.S. Pat. No. 5,869,441), having good chelating and lathering properties, and low ocular irritancy. See e.g., U.S. Pat. No. 6,503,873.

In some embodiments, the presently disclosed subject matter relates to a method of preparing N-acyl-N,N',N'-alkylenediamine trialkanoic acids that comprises the use of triester intermediates. For example, the presently disclosed subject matter can relate to a method of preparing N-acyl-N,N',N'-ethylenediamine trialkanoic acids, wherein the method can comprise providing a 2-substituted imidazoline compound (e.g., a 2-alkylimidazoline) and contacting the 2-substituted-imidazoline compound with an ester of a haloalkanoic acid to provide a N-acyl-N,N',N'-ethylenediamine trialkanoic acid ester. The triesters can then be hydrolyzed to provide the triacids. Thus, in some of the presently disclosed methods, an alkyl substituent of a 2-substituted imidazoline or analog thereof can provide the N-acyl group of the final N-acyl-N, N',N'-alkylenediamine triester or triacid. The presently disclosed methods can provide the triesters and triacids in high yield and purity. The addition of the acid-forming moieties in ester form alleviates the need for manipulation and/or purification of highly polar carboxylic acid and carboxylate intermediates.

In some embodiments, the presently disclosed subject matter provides methods of preparing N-acyl-N,N',N'-alkylenediamine trialkanoic acid esters. The two amine groups of the diamine portion of the compounds can be linked, for example, by methylene, ethylene, propylene, butylene, pentylene, or longer groups. Accordingly, in some embodiments, the presently disclosed subject matter provides a method of preparing a compound of Formula (I):

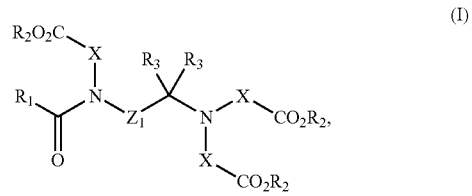

(I)

wherein:

Z$_1$ can be present or absent and when present is —[C(R$_4$)$_2$]$_m$—;

m is an integer from 1 to 4;

each X is —CHR$_5$—[C(R$_6$)$_2$]$_n$—;

each n is independently an integer from 0 to 4;

R$_1$ is selected from the group comprising H, alkyl, cycloalkyl, substituted alkyl, aralkyl, aryl, and substituted aryl;

each R$_2$ is independently selected from the group comprising alkyl, cycloalkyl, substituted alkyl, aralkyl, aryl, and substituted aryl;

each R$_3$ and each R$_4$ are independently selected from the group comprising H, alkyl, cycloalkyl, substituted alkyl, aralkyl, aryl, and substituted aryl, or wherein one R$_3$ and one R$_4$ are together alkylene, substituted alkylene, aralkylene, or substituted aralkylene, or wherein two R$_4$ are together alkylene, substituted alkylene, aralkylene, or substituted aralkylene;

each R$_5$ is selected from the group comprising H, alkyl, cycloalkyl, substituted alkyl, aralkyl, aryl, and substituted aryl; and each $R_6$ is independently selected from the group comprising H, alkyl, alkoxy, cycloalkyl, aralkyl, aralkoxy, aryloxy, aryl, and substituted aryl; wherein the method comprises:

providing a cyclic amidine compound wherein the cyclic amidine compound is a cyclic amidine wherein the amidine nitrogen atoms are linked via an alkylene or aralkylene group; and contacting the cyclic amidine compound with an ester of a haloalkanoic acid in the presence of a base.

In some embodiments, $R_1$ is not H. For example, in some embodiments, $R_1$ is selected from the group comprising alkyl, cycloalkyl, substituted alkyl, aralkyl, aryl, and substituted aryl.

In some embodiments, the cyclic amidine compound is a compound of Formula (II)

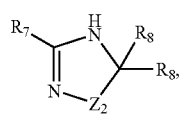

(II)

wherein:

$Z_2$ can be present or absent and when present is —[C($R_9$)$_2$]$_m$—;

m is an integer from 1 to 4;

$R_7$ is selected from the group comprising alkyl, cycloalkyl, substituted alkyl, aralkyl, aryl and substituted aryl; and each $R_8$ and each $R_9$ are independently selected from the group comprising H, alkyl, cycloalkyl, substituted alkyl, aralkyl, aryl and substituted aryl, or wherein one $R_8$ and one $R_9$ together are alkylene, substituted alkylene, aralkylene, or substituted aralkylene, or wherein two $R_9$ together are alkylene, substituted alkylene, aralkylene, or substituted aralkylene.

In some embodiments, $Z_2$ is present and m can be 1, 2, 3, or 4. In some embodiments, $Z_2$ is absent and the nitrogen atoms of the cyclic amidine of Formula (II) are linked by a methylene or substituted methylene group (i.e. —C($R_8$)$_2$—).

In some embodiments, $Z_2$ is present and m is 1 and the cyclic amidine compound is a 2-substituted imidazoline.

In some embodiments, the presently disclosed subject matter provides a method of preparing a compound of Formula (I) wherein the compound of Formula (I) is a compound of Formula (Ia):

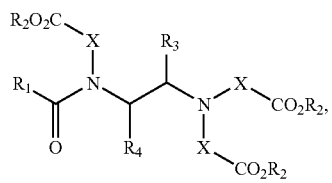

(Ia)

wherein:

each X is —CHR$_5$—[C($R_6$)$_2$]$_n$—;

each n is independently an integer from 0 to 4;

$R_1$ is selected from the group comprising alkyl, cycloalkyl, substituted alkyl, aralkyl, aryl, and substituted aryl;

each $R_2$ is independently selected from the group comprising alkyl, cycloalkyl, substituted alkyl, aralkyl, aryl, and substituted aryl;

$R_3$ and $R_4$ are independently selected from the group comprising H, alkyl, cycloalkyl, substituted alkyl, aralkyl, aryl, and substituted aryl, or wherein $R_3$ and $R_4$ together are alkylene, substituted alkylene, aralkylene, or substituted aralkylene;

each $R_5$ is selected from the group comprising H, alkyl, cycloalkyl, substituted alkyl, aralkyl, aryl, and substituted aryl; and each $R_6$ is independently selected from the group comprising H, alkyl, alkoxy, cycloalkyl, aralkyl, aralkoxy, aryloxy, aryl, and substituted aryl; wherein the method comprises:

providing a 2-substituted imidazoline; and contacting the 2-substituted imidazoline with an ester of a haloalkanoic acid in the presence of a base.

In some embodiments. $R_1$ is alkyl (e.g., straight-chain or branched alkyl, or saturated or unsaturated alkyl). In some embodiments. $R_1$ is alkenyl (i.e., comprises one or more carbon-carbon double bonds). In some embodiments, $R_1$ is saturated alkyl. For example, $R_1$ can be a straight-chain, saturated alkyl group, such as, but not limited to, methyl, ethyl, propyl, n-butyl, pentyl, hexyl, heptyl, octyl, nonyl, decyl, undecyl, dodecyl, and the like. In some embodiments. $R_1$ can be a branched alkyl group, such as, but not limited to, isopropyl, isobutyl, sec-butyl, tert-butyl, isopentyl, and neopentyl, and the like.

In some embodiments. $R_1$ can include a point of unsaturation or a substituent or branch point at the carbon directly attached to the carbonyl carbon (i.e., the α-carbon). Thus, in some embodiments. $R_1$ can have a structure such as one of:

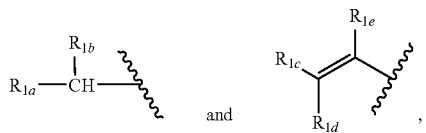

wherein $R_{1a}$ and $R_{1b}$ are independently selected from the group comprising alkyl, substituted alkyl, cycloalkyl, aralkyl, aryl, and substituted alkyl, and wherein $R_{1c}$, $R_{1d}$ and $R_{1e}$ are independently selected from the group comprising H, alkyl, substituted alkyl, cycloalkyl, aralkyl, aryl, and substituted alkyl.

The $R_1$ alkyl group can comprise 1-20 carbon atoms. In some embodiments, the alkyl is C1-C12 alkyl (i.e., C1-C2, C3, C4, C5, C6, C7, C8, C9, C10, C11 or C12 alkyl). In some embodiments, the alkyl is C8 alkyl.

In some embodiments, $R_2$ is lower alkyl (i.e., C1-C6 alkyl). Thus, $R_2$ can be selected from the group including, but not limited to, methyl, ethyl, isopropyl, n-propyl, n-butyl, sec-butyl, iso-butyl, tert-butyl, pentyl, iso-pentyl, neo-pentyl, and hexyl. In some embodiments, each $R_2$ is the same. In some embodiments, $R_2$ is ethyl.

In some embodiment, both of $R_3$ and $R_4$ are H. In some embodiments, at least one of $R_3$ and $R_4$ is not H. In some embodiments, both $R_3$ and $R_4$ are not H. In some embodiments. $R_3$ and $R_4$ are independently selected from H and alkyl. In some embodiments, one of $R_3$ and $R_4$ is alkyl. In some embodiments, both $R_3$ and $R_4$ are alkyl.

In some embodiments. $R_3$ and $R_4$ together are alkylene, substituted alkylene, aralkylene, or substituted aralkylene. For example, $R_3$ and $R_4$ together can be selected from the group including, but not limited to, xylenylene (i.e., —CH$_2$—C$_6$H$_4$—CH$_2$—), napthylenedimethylene (i.e., —CH$_2$—C$_{10}$H$_6$—CH$_2$—), methylene (i.e., —CH$_2$—), ethylene (i.e., —(CH$_2$)$_2$—), propylene (i.e., —CH$_2$CH$_2$CH$_2$—), butylene (i.e., —(CH$_2$)$_4$—), butenylene (e.g., —CH$_2$—CH═CH—

CH$_2$—), pentylene (i.e., —(CH$_2$)$_5$—), and cyclohexylenedimethylene (i.e., —CH$_2$—C$_6$H$_{10}$—CH$_2$—).

In some embodiments, n is 0 and X is —CHR$_5$—. In some embodiments. R$_5$ is selected from the group including H and alkyl.

Suitable 2-substituted imidazolines for use according to the presently disclosed subject matter can have a structure of Formula (IIa):

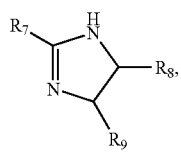
(IIa)

wherein:

R$_7$ is selected from the group comprising alkyl, cycloalkyl, substituted alkyl, aralkyl, aryl and substituted aryl; and R$_8$ and R$_9$ are independently selected from the group comprising H, alkyl, cycloalkyl, substituted alkyl, aralkyl, aryl and substituted aryl, or wherein R$_8$ and R$_9$ together are alkylene, substituted alkylene, aralkylene, or substituted aralkylene.

In some embodiments, R$_7$ is alkyl (e.g., straight-chain or branched alkyl, or saturated or unsaturated alkyl). In some embodiments, R$_7$ is saturated alkyl. For example, R$_7$ can be a straight-chain, saturated alkyl group, such as, but not limited to, methyl, ethyl, propyl, n-butyl, pentyl, hexyl, heptyl, octyl, nonyl, decyl, undecyl, dodecyl, and the like. In some embodiments, R$_7$ is a branched alkyl group, such as, but not limited to, isopropyl, isobutyl, sec-butyl, tert-butyl, isopentyl, and neopentyl, and the like.

In some embodiments. R$_7$ can include a point of unsaturation or a substituent or branch point at the carbon directly attached to the imidazoline ring. Thus, in some embodiments, R$_7$ can have a structure such as one of:

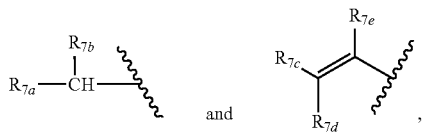
and wherein R$_{7a}$ and R$_{7b}$ are independently selected from the group comprising alkyl, substituted alkyl, cycloalkyl, aralkyl, aryl, and substituted alkyl, and wherein R$_7$, R$_{7d}$ and R$_{7e}$ are independently selected from the group comprising H, alkyl, substituted alkyl, cycloalkyl, aralkyl, aryl, and substituted alkyl.

Thus, in some embodiments, the compound of Formula (IIa) can have a structure of one of Formulas (IIaa) and (IIab):

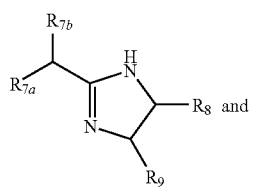
(IIaa)

and

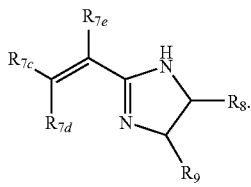
(IIab)

The R$_7$ alkyl group can comprise 1-20 carbon atoms. In some embodiments, the alkyl is C1-C12 alkyl (i.e., C1, C2, C3, C4, C5, C6, C7, C8, C9, C10, C11 or C12 alkyl). In some embodiments, the alkyl is C8 alkyl.

In some embodiments, at least one of R$_8$ and R$_9$ is not H. In some embodiments, both R$_8$ and R$_9$ are not H.

In some embodiments, R$_5$ and R$_9$ are independently selected from H and alkyl. In some embodiments, both of R$_5$ and R$_9$ are H. In some embodiments, one of R$_8$ and R$_9$ is alkyl. In some embodiments, both R$_5$ and R$_9$ are alkyl. In some embodiments, the alkyl is C1-C6 alkyl. In some embodiments, the alkyl is methyl.

In some embodiments, R$_8$ and R$_9$ together are alkylene, substituted alkylene, aralkylene, or substituted aralkylene. For example, R$_8$ and R$_9$ together can be selected from the group including, but not limited to, xylenylene (i.e., —CH$_2$—C$_6$H$_4$—CH$_2$—), napthylenedimethylene (i.e., —CH$_2$—C$_{10}$H$_6$—CH$_2$—), methylene (i.e., —CH$_2$—), ethylene (i.e., —(CH$_2$)$_2$—), propylene (i.e., —CH$_2$CH$_2$CH$_2$—), butylene (i.e., —(CH$_2$)$_4$—), butenylene (e.g., —CH$_2$—CH=CH—CH$_2$—), pentylene (i.e., —(CH$_2$)$_5$—), and cyclohexylenedimethylene (i.e., —CH$_2$—C$_6$H$_{10}$—CH$_2$—). In some embodiments, R$_8$ and R$_9$ together are alkylene or aralkylene and the compound of Formula (IIa) can have a structure of, for example, one of Formulas (IIac), (IIad), (IIae), and (IIaf):

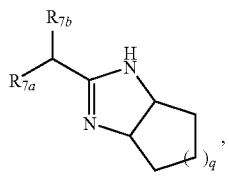
(IIac)

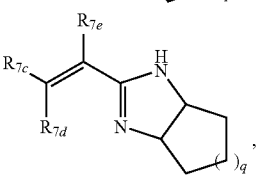
(IIad)

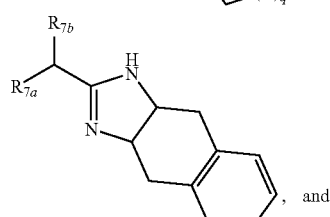
(IIae)

, and

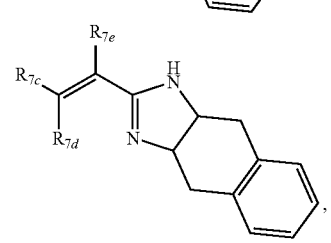
(IIaf)

wherein q can be an integer between 0 and 4 (i.e., 0, 1, 2, 3, or 4); wherein R$_{7a}$ and R$_{7b}$ are independently selected from the group comprising alkyl, substituted alkyl, cycloalkyl, aralkyl, aryl, and substituted alkyl, and wherein $R_{7c}$ $R_{7d}$ and $R_{7e}$ are independently selected from the group comprising H, alkyl, substituted alkyl, cycloalkyl, aralkyl, aryl, and substituted alkyl.

Compounds of Formula (II) (e.g., the compounds of Formula (IIa)) can be prepared by reaction of a suitable carboxylic acid (e.g., a fatty acid, such as, but not limited to, lauric acid, myristic acid, palmitic acid, stearic acid, oleic acid, linoleic acid, linolenic acid, arachidonic acid, eleostearic acid, and the like) and ethylenediamine or an analog thereof (such as 1,2-propanediamine, 1,2-butanediamine, 1,2-cyclopropanediamine, or 1,2-hexanediamine, 1,3-propanediamine, 1,4-butanediamine, and the like). The compound of Formula (II) can also be prepared by any other suitable method known in the art (e.g., the reaction of an ethylenediamine (or other diamine) and an aldehyde). In some embodiments, the compound of Formula (II) can be purchased from a suitable source.

In some embodiments, the ester is the ester of a haloacetic acid, a halopropanoic acid, or a halobutanoic acid. In some embodiments, the ester is the ester of an α-haloalkanoic acid. In some embodiments, the ester is a methyl or ethyl ester. In some embodiments, the ester is a mixture of different esters. In some embodiments, the ester is ethyl chloroacetate, ethyl bromoacetate, or a mixture thereof.

Typically between about 3 and about 4 molar equivalents (eq.) of the ester is contacted with the cyclic amidine (e.g., the 2-substituted imidazoline). In some embodiments, between about 3 and about 3.5 molar equivalents (e.g., about 3.00, 3.05, 3.10, 3.15, 3.20, 3.25, 3.30, 3.35, 3.40, 3.45, or 3.50 eq.) of ester are contacted with the cyclic amidine (e.g., the 2-substituted imidazoline). However, more equivalents (or slightly fewer equivalents) can also be used, if desired, for example, depending upon the relative cost and/or availability of the cyclic amidine (e.g., the 2-substituted imidazoline) and ester reagents and/or the desired reaction time. In some embodiments, the progress of the reaction can be monitored as described further hereinbelow and additional ester or cyclic amidine (e.g., the 2-substituted imidazoline) can be added as needed to increase the yield of the compound of Formula (I).

Any suitable solvent can be used. Solvent choice can depend upon the solubility of the cyclic amidine (e.g., the 2-substituted imidazoline) and/or the ester and/or upon the boiling point of the solvent (which can affect the maximum temperature at which the cyclic amidine (e.g., the 2-substituted imidazoline) can be contacted with the ester). Typically the solvent comprises an aprotic, non-polar solvent or a mixture of aprotic, non-polar solvents. Suitable aprotic, non-polar solvents include, but are not limited to, ethyl acetate; carbon disulphide; ethers, such as, diethyl ether, tetrahydrofuran (THF), ethylene glycol dimethyl ether, dibutyl ether, diphenyl ether, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. In some embodiments, the solvent comprises an aromatic solvent, such as, but not limited to toluene or benzene.

In some embodiments, the contacting can take place at between about 0° C. and about 200° C. In some embodiments, the contacting can take place between about room temperature (e.g., about 20° C.) and about 140° C. (e.g., about 20, 25, 30, 35, 40, 45, 50, 55, 60, 65, 70, 75, 80, 85, 90, 95, 100, 105, 110, 115, 120, 125, 130, 135, or 140° C.). In some embodiments, the contacting can take place between about 80° C. and about 120° C. In some embodiments, the contacting takes place at about 100° C.

As noted hereinabove, the reaction between the cyclic amidine (e.g., the 2-substituted imidazoline) and the ester can be monitored by any suitable method. For example, the reaction can be monitored via any suitable chromatography (e.g., gas chromatography (GC), thin-layer chromatography (TLC), or high performance liquid chromatography (HPLC)) and/or spectroscopy techniques (e.g., mass spectroscopy (MS), nuclear magnetic resonance spectroscopy (NMR), infrared spectroscopy (IR), or ultraviolet (UV) spectroscopy) known in the art of organic synthesis. The reaction can be allowed to continue for a particular period of time or until the monitoring method indicates that one or more of the starting materials (i.e., the cyclic amidine and the ester) are no long present or that no additional compound of Formula (I) is being produced. The contacting can take place for any suitable period of time. In some embodiments, the contacting takes place for between about 10 minutes and about 48 hours. In some embodiments, the contacting takes place for about 4 to about 12 hours (e.g., about 4, 5, 6, 7, 8, 9, 10, 11, or 12 hours). In some embodiments, the contacting is for about 8 hours.

Any suitable base can be used. Typically, the base will be a poor nucleophile, but has the ability to accept a proton to neutralize any acid formed during the contacting step. Suitable non-nucleophilic or poorly nucleophilic bases include, but are not limited to, carbonate salts, such as sodium carbonate, potassium carbonate, sodium bicarbonate, and the like; trialkylamines, such as triethylamine (TEA), and diisopropylethylamine; alkali metal tert-butoxides (e.g., sodium tert-butoxide); 1,8-diazabicycloundec-7-ene (DBU); sodium or potassium bis(trimethylsilylamide); lithium disopropylamide (LDA); and the like. In some embodiments, the base is a carbonate salt. In some embodiments, the base is sodium bicarbonate.

In some embodiments, between about 2.5 and about 6 molar equivalents of base (relative to moles of cyclic amidine) can be used. In some embodiments, between about 4 and about 5 molar equivalents of base are used.

In some embodiments, the compound of Formula (I) can be hydrolyzed to a triacid or salt thereof. Thus, in some embodiments, the presently disclosed subject matter provides a method of preparing a N-acyl-N,N',N'-alkylenediamine trialkanoic acid or salt thereof, wherein the method comprises providing a cyclic amidine compound wherein the cyclic amidine compound is a cyclic amidine wherein the amidine nitrogen atoms are linked via an alkylene or aralkylene group;

contacting the cyclic amidine compound with an ester of a haloalkanoic acid in the presence of a first base of provide a compound of Formula (I); and contacting the compound of Formula (I) with a second base.

In some embodiments, the presently disclosed subject matter provides a method of making a N-acyl-ethylenediamine-N,N',N'-trialkanoic acid or a salt thereof using a compound of Formula (Ia) as a synthetic intermediate. Accordingly, in some embodiments, the presently disclosed subject matter provides a method that can comprise:

providing a 2-substituted imidazoline;

contacting the 2-substituted imidazoline with an ester of a haloalkanoic acid in the presence of a first base to provide a compound of Formula (Ia):

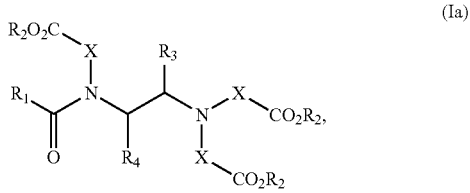

wherein:
each X is —CHR$_5$—[C(R$_6$)$_2$]$_n$—;
each n is independently an integer between 0 and 4;
R$_1$ is selected from the group comprising alkyl, cycloalkyl, substituted alkyl, aralkyl, aryl, and substituted aryl;
each R$_2$ is independently selected from the group comprising alkyl, cycloalkyl, substituted alkyl, aralkyl, aryl, and substituted aryl;
R$_3$ and R$_4$ are independently selected from the group comprising H, alkyl, cycloalkyl, substituted alkyl, aralkyl, aryl, and substituted aryl, or wherein R$_3$ and R$_4$ together are alkylene, substituted alkylene, aralkylene, or substituted aralkylene;
each R$_5$ is selected from the group comprising H, alkyl, cycloalkyl, substituted alkyl, aralkyl, aryl and substituted aryl; and
each R$_6$ is independently selected from the group comprising H, alkyl, alkoxy, cycloalkyl, aralkyl, aralkoxy, aryloxy, aryl, and substituted aryl; and
contacting the compound of Formula (Ia) with a second base, thereby forming the N-acyl-N,N',N'-ethylenediamine trialkanoic acid or salt thereof.

In some embodiments, the ester of the haloalkanoic acid is the ester of an α-haloalkanoic acid and n is 0. In some embodiments, at least one of R$_3$ and R$_4$ is not H.

In some embodiments, the second base is an alkali metal hydroxide, such as sodium, potassium, cesium, or lithium hydroxide. In some embodiments, the alkali metal hydroxide is provided in an aqueous solution. Thus, in some embodiments, the compound of Formula (I) (e.g., the compound of Formula (Ia)) is dissolved in a solvent that is miscible with water, such as acetonitrile or an alcohol (e.g., methanol, ethanol, propanol, butanol, or the like), or a solvent mixture comprising a water soluble solvent or solvents. Then, an aliquot of the base-containing aqueous solution can be added and the resulting mixture allowed to mix for a period of time. The mixing can be performed, for example, by stirring or shaking.

Typically, about 3 molar equivalents or more of the second base are added. Thus, in some embodiments, at least about 3.0, 3.1, 3.2, 3.3, 3.4, 3.5, 3.6, 3.7, 3.8, 3.9, 4.0, 4.5, or 5.0 molar equivalents of the second base are added. Conditions related to the addition of the second base can be controlled such that the contacting pH is about 10 or greater. In some embodiments, the contacting pH is controlled to be between about 11 and 13 (e.g., about 11, 12, or 13). If desired, the mixture of the compound of Formula (I) or Formula (Ia) and the second base can be heated. However, in some embodiments, the contacting is performed without adding external heat. The reaction of the second base and the compound of Formula (I) or Formula (Ia) can be followed by chromatography and/or spectroscopy techniques known in the art (e.g., GC, TLC, HPLC, MS, NMR, IR, and/or UV) to monitor the formation of products and/or the disappearance of the compound of Formula (I) or Formula (Ia).

In some embodiments, the mixing proceeds for about 0.5 to about 12 hours. In some embodiments, the mixing takes place for about 1 to about 5 hours (e.g., about 1, 2, 3, 4, or 5 hours). In some embodiments, the mixing proceeds for about 2 hours.

Following mixing for a period of time, the mixture can be acidified. For example, any suitable acid can be added to lower the pH of the mixture sufficiently to protonate the carboxylate groups formed by mixing the compound of Formula (I) or Formula (Ia) with the second base. In some embodiments, the acid is a strong acid (i.e., an acid having a pK$_a$ of <about 1). Suitable acids include, but are not limited to, hydrochloric acid (HCl), hydroiodic acid (HI), hydrobromic acid (HBr), sulfuric acid (H$_2$SO$_4$), HClO$_4$, HNO$_3$, chloric acid, bromic acid, perbromic acid, iodicacid, periodic acid, triflic acid, and fluorosulfuric acid. In some embodiments, the pH of the mixture is lowered to about 3 or less (e.g., about 3, about 2.5, about 2).

In some embodiments, the presently disclosed subject matter provides a method of preparing a N-acyl-N,N',N'-ethylenediamine triacetic acid ester as shown in Scheme 1, below. For example, the compound can be prepared by first preparing a suitable 2-substituted imidazoline, 3, (e.g., a 2-alkyl imidazoline wherein R is alkyl) by the reaction of ethylenediamine, 2, and a carboxylic acid, 1, as shown in Step 1 of Scheme 1. The 2-substituted imidazoline, 3, can be reacted with a haloacetic acid ester, such as a chloroacetic acid ester, 4, as shown in Step 2 of Scheme 1 to form N-acyl-N,N',N'-ethylenediamine triacetic acid ester, 5. Step 2 can also be performed in the presence of a base, such as sodium bicarbonate, to neutralize acid (e.g., HCl, formed during the reaction). The reaction shown in Step 2 can be performed such as to allow for quantitative or near quantitative conversion of 2-substituted imidazoline 3 to ester 5.

Scheme 1. Synthesis of N-Acyl-N,N',N'-Ethylenediamine Triacetate Esters.

Step 1:

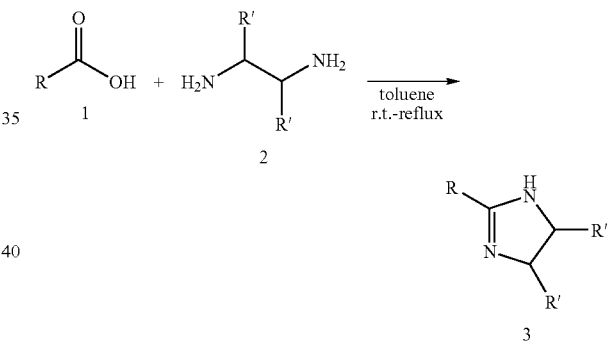

Step 2:

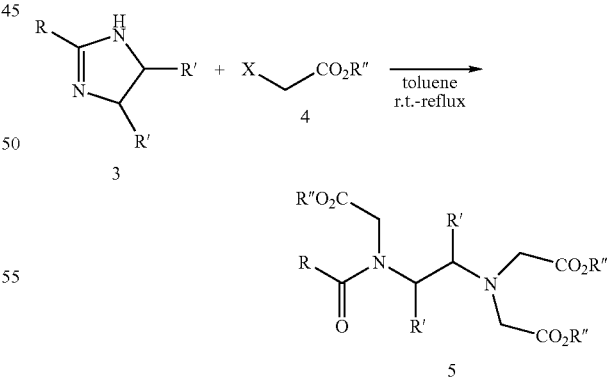

As shown in Scheme 2, if desired, N-acyl-N,N',N'-ethylenediamine triacetic acid ester 5 can be hydrolyzed under basic conditions (e.g., with alkali metal hydroxide XOH) to form N-acyl-N,N',N'-ethylenediamine triacetate salt, 6. Suitable alkali metal hydroxides include, for example sodium, cesium, lithium, or potassium hydroxide. The triacetate can be protonated, if desired, with an acid (e.g., with HCl, HBr, H$_2$SO$_4$, etc.) to form a triacetic acid.

Scheme 2. Synthesis of N-Acyl-N,N',N'-Ethylenediamine Triacetate Salts.

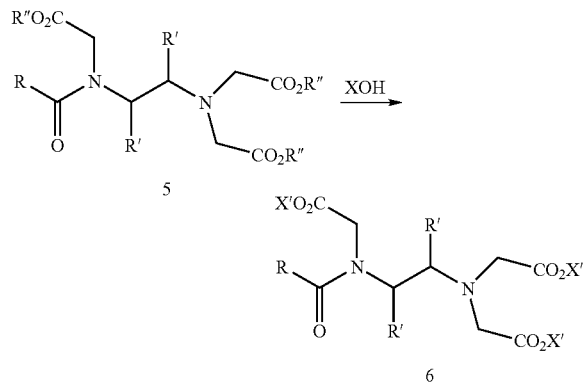

III. COMPOUNDS AND COMPOSITIONS

The compounds of Formula (I) (including the compounds of Formula (Ia) can be used as chelating agents to sequester cations, such as metal cations. The term "chelating agent" refers to a molecule or molecular ion having an unshared electron pair available for donation to a cation. Thus, in some embodiments, compounds of Formula (I) can chelate ions via interactions with the unshared electron pairs of the ester oxygen atoms and/or the nitrogen atoms of the ethylenediamine-based group. Chelating agents can be useful, for example, in the preparation of metal cation contrast agents used in medical imaging and in removing metal cations from synthetic reaction mixtures, from environmental (soil or water) samples, or from a subject (e.g., a subject in need of the removal a toxic metal cation). In some embodiments, the compounds of Formula (I) can also find use as synthetic intermediates in the synthesis of N-acyl-N,N', N'-alkylenediamine trialkanoic acids or salts thereof. Such N-acyl-N,N', N'-alkylenediamine trialkanoic acids and their salts are useful as chelating agents (e.g. as oil soluble chelators) and as amphoteric and/or anioinic surfactants, for example, in detergents. Such compounds can also be useful as corrosion inhibitors, lubricant enhancers, enzyme inhibitors, metal precipitation additives, and emulsifiers, among other things. See e.g., U.S. Pat. No. 5,284,972.

Accordingly, in some embodiments, the presently disclosed subject matter provides compounds of Formula (I) as described hereinabove and compositions comprising the compounds of Formula (I). In some embodiments, the presently disclosed subject matter provides a compound of Formula (I):

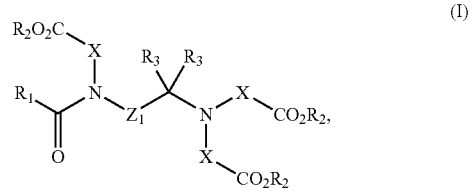

wherein:

$Z_1$ can be present or absent and when present is —[C$(R_4)_2$]$_m$—;

m is an integer from 1 to 4;

each X is —CHR$_5$—[C(R$_6$)$_2$]$_n$—;

each n is independently an integer from 0 to 4;

$R_1$ is selected from the group consisting of H, alkyl, cycloalkyl, substituted alkyl, aralkyl, aryl, and substituted aryl;

each $R_2$ is independently selected from the group consisting of alkyl, cycloalkyl, substituted alkyl, aralkyl, aryl, and substituted aryl;

each $R_3$ and each $R_4$ are independently selected from the group consisting of H, alkyl, cycloalkyl, substituted alkyl, aralkyl, aryl, and substituted aryl, or wherein one $R_3$ and one $R_4$ are together alkylene, substituted alkylene, aralkylene, or substituted aralkylene, or wherein two $R_4$ are together alkylene, substituted alkylene, aralkylene, or substituted aralkylene;

each $R_5$ is selected from the group consisting of H, alkyl, cycloalkyl, substituted alkyl, aralkyl, aryl, and substituted aryl; and each $R_6$ is independently selected from the group consisting of H, alkyl, alkoxy, cycloalkyl, aralkyl, aralkoxy, aryloxy, aryl, and substituted aryl;

subject to the proviso that when $Z_1$ is present and m is 1, at least one $R_3$ or one $R_4$ is not H.

In some embodiments, $R_1$ is not H. In some embodiments, $Z_1$ is present. In some embodiments, m is 1. In some embodiments, the compound of Formula (I) is a compound of Formula (Ia):

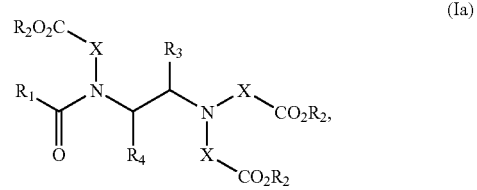

wherein:

each X is —CHR$_5$—[C(R$_6$)$_2$]$_n$—, each n is independently an integer from 0 to 4;

$R_1$ is selected from the group comprising alkyl, cycloalkyl, substituted alkyl, aralkyl, aryl, and substituted aryl;

each $R_2$ is independently selected from the group comprising alkyl, cycloalkyl, substituted alkyl, aralkyl, aryl, and substituted aryl;

$R_3$ and $R_4$ are independently selected from the group comprising H, alkyl, cycloalkyl, substituted alkyl, aralkyl, aryl, and substituted aryl, or wherein $R_3$ and $R_4$ together are alkylene, substituted alkylene, aralkylene, or substituted aralkylene, subject to the proviso that at least one of $R_3$ and $R_4$ is not H;

each $R_5$ is selected from the group comprising H, alkyl, cycloalkyl, substituted alkyl, aralkyl, aryl and substituted aryl; and each $R_6$ is independently selected from the group comprising H, alkyl, alkoxy, cycloalkyl, aralkyl, aralkoxy, aryloxy, aryl, and substituted aryl.

In some embodiments, n is 0. In some embodiments, $R_5$ is H or alkyl. In some embodiments, each $R_2$ is methyl, ethyl, propyl, or isopropyl.

In some embodiments, the compound of Formula (Ia) is:

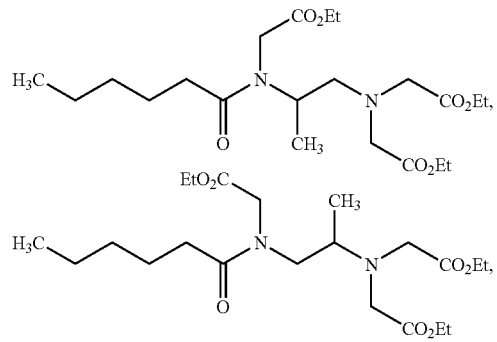

or a mixture thereof.

In some embodiments, the presently disclosed subject matter provides a composition comprising a compound of Formula (I) (e.g., a compound of Formula (Ia)). For example, the composition can comprise one or more compounds of Formula (I) in a carrier (e.g., a solvent) suitable for the desired use of the composition. Thus, in some embodiments, the compositions can include one or more compound of Formula (I) in a suitable carrier (e.g., water, a buffer, an alcohol, or mixtures thereof). In some embodiments, such as when the compound of Formula (I) is used as a chelating agent for a medical diagnostic contrast agent or as a chelating agent to remove toxic metals from a subject (e.g., a mammal), the compositions can comprise a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals, and more particularly in humans. In some embodiments, the term "pharmaceutically acceptable carrier" refers to a diluent, adjuvant, excipient, or delivery vehicle that is pharmaceutically acceptable in humans and in which the compound can be administered to a subject (e.g., orally, intravenously, topically, interperitoneally, etc.). In some embodiments, such as in contrast agent-containing compositions, the composition can further include one or more metal cations (e.g., paramagentic metal ions).

Compounds of Formula (I) (e.g., compounds of Formula (Ia)) can also be useful as nonionic surfactants. In some embodiments, the compositions comprising one or more compound of Formula (I) can be used as, for example, shampoos, bath gels, bar soaps, hair conditioning products, contact lens conditioning products, skin conditioning products (e.g., skin creams or lotions), make-up removal compositions, and/or household or industrial cleaners (e.g., dish-washing or laundry detergent), and the like. The compositions can also include additional agents, such as anti-microbial agents, additional detergents, emulsifying agents, preservatives, thickening agents, pH controlling agents, emollients (e.g., fats and/or oils), coloring agents, fragrances, and/or alcohols.

In some embodiments, the presently disclosed subject matter provides a compound of Formula (III):

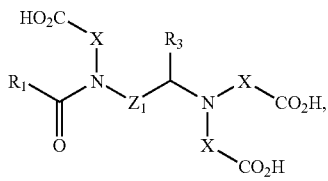

wherein:
$Z_1$ can be present or absent and when present is $-[C(R_4)_2]_m-$;
m is an integer from 1 to 4;
each X is $-CHR_5-[C(R_6)_2]_n-$;
each n is independently an integer from 0 to 4;
$R_1$ is selected from the group comprising H, alkyl, cycloalkyl, substituted alkyl, aralkyl, aryl, and substituted aryl;
each $R_2$ is independently selected from the group comprising alkyl, cycloalkyl, substituted alkyl, aralkyl, aryl, and substituted aryl;
each $R_3$ and each $R_4$ are independently selected from the group comprising H, alkyl, cycloalkyl, substituted alkyl, aralkyl, aryl, and substituted aryl, or wherein one $R_3$ and one $R_4$ are together alkylene, substituted alkylene, aralkylene, or substituted aralkylene, or wherein two $R_4$ are together alkylene, substituted alkylene, aralkylene, or substituted aralkylene;

each $R_5$ is selected from the group comprising H, alkyl, cycloalkyl, substituted alkyl, aralkyl, aryl, and substituted aryl; and
each $R_6$ is independently selected from the group comprising H, alkyl, alkoxy, cycloalkyl, aralkyl, aralkoxy, aryloxy, aryl, and substituted aryl; or a salt thereof, and subject to the proviso that when $Z_1$ is present and m is 1, at least one $R_3$ or one $R_4$ is not H.

In some embodiments, $R_1$ is not H. In some embodiments, $Z_1$ is present. In some embodiments, m is 1. In some embodiments, the compound of Formula (III) is a compound of Formula (IIIa):

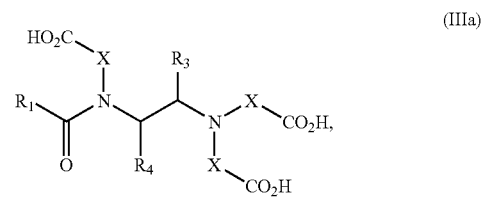

wherein:
each X is $-CHR_5-[C(R_6)_2]_n-$;
each n is independently an integer from 0 to 4;
$R_1$ is selected from the group comprising alkyl, cycloalkyl, substituted alkyl, aralkyl, aryl, and substituted aryl;
each $R_2$ is independently selected from the group comprising alkyl, cycloalkyl, substituted alkyl, aralkyl, aryl, and substituted aryl;
$R_3$ and $R_4$ are independently selected from the group comprising H, alkyl, cycloalkyl, substituted alkyl, aralkyl, aryl, and substituted aryl, or wherein $R_3$ and $R_4$ together are alkylene, substituted alkylene, aralkylene, or substituted aralkylene; subject to the proviso that one or both of $R_3$ and $R_4$ are not H;
each $R_5$ is selected from the group comprising H, alkyl, cycloalkyl, substituted alkyl, aralkyl, aryl, and substituted aryl; and
each $R_6$ is independently selected from the group comprising H, alkyl, alkoxy, cycloalkyl, aralkyl, aralkoxy, aryloxy, aryl, and substituted aryl;
or a salt thereof.

In some embodiments, each n is 0. In some embodiments, $R_5$ is H or alkyl.

In some embodiments, the compound of Formula (IIIa) is

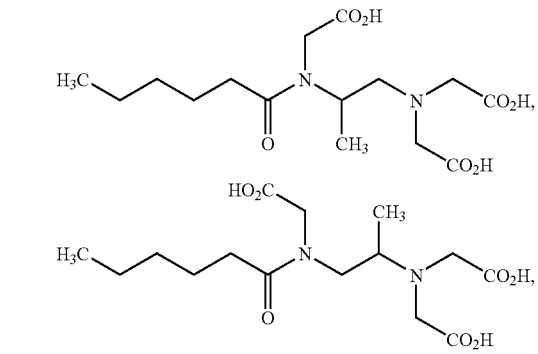

or a salt or mixture thereof.

In some embodiments, the presently disclosed subject matter provides a composition comprising a compound of Formula (III) (e.g., a compound of Formula (IIIa)) or a salt thereof. The compositions can include one or more compound of Formula (III) in a suitable carrier (e.g., water, a buffer, an alcohol, or mixtures thereof). For example, compositions can include, but are not limited to, shampoos, bath gels, bar soaps, hair conditioning products, contact lens conditioning products, skin conditioning products (e.g., skin creams or lotions), make-up removal compositions, and household or industrial cleaners (e.g., dish-washing or laundry detergent). The compositions can also include additional agents, such as anti-microbial agents, additional detergents, emulsifying agents, preservatives, thickening agents, pH controlling agents, emollients (e.g., fats and/or oils), coloring agents, fragrances, and/or alcohols.

EXAMPLES

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Example 1

N-Nonanoyl-Ethylenediamine-N,N'N'-Triacetic Acid Ethyl Triester, 5a

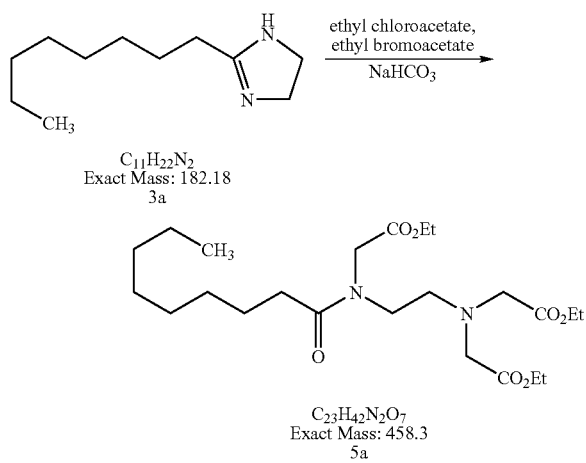

A 1.0 L 3-necked flask was charged under nitrogen atmosphere with 190 mL of toluene, 95.10 g (0.522 mol) 2-octylimidazoline, 3a, 220 g (2.61 mol) sodium bicarbonate, 179.12 g (1.462 mol) ethyl chloroacetate, and 43.60 g (0.261 mol) ethyl bromoacetate. The mixture was heated to 100° C. for 8 hrs and HPLC analysis indicated complete reaction. The reaction mixture was allowed to cool to ambient temperature. The solids were removed by filtration and washed with 95 mL of toluene. The combined filtrates were concentrated to dryness to afford 251 g (100% yield) of crude liquid, the triester 5a. $^1$H NMR (400 MHz, CDCl$_3$) 4.17-4.02 (m, 8H), 3.47 (s, 4H), 3.46-3.41 (m, 2H), 2.88-2.86 (m, 2H), 2.34-2.11 (m, 2H), 1.61-1.50 (m, 2H), 1.36-1.04 (m, 19H), 0.92-0.79 (m, 3H); LC-MS, m/z calcd for C$_{23}$H$_{42}$N$_2$O$_7$: 458.3. found (M+1)$^+$ 459.3.

Example 2

N-Hexanoyl-Ethylenediamine-N,N'N'-Triacetic Acid Ethyl Triester, 5b

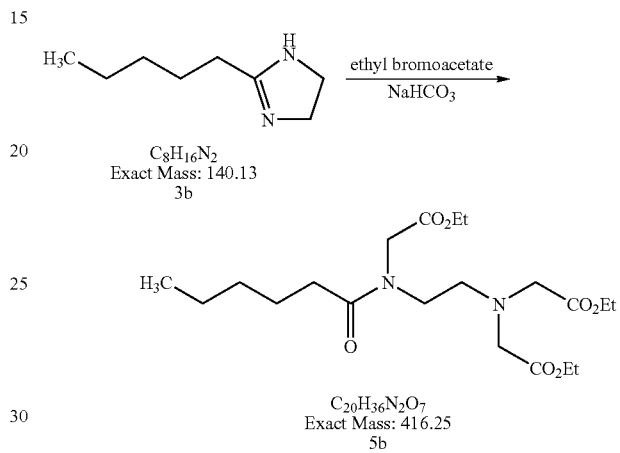

A 250 mL 3-necked flask was charged under nitrogen atmosphere with 28 mL of toluene, 14 g (0.10 mol) 2-pentylimidazoline, 3b, 42.0 g (0.5 mol) sodium bicarbonate and 38.7 mL (0.35 mol) ethyl bromoacetate. The mixture was heated to 100° C. for 8 hrs and HPLC analysis indicated complete reaction. The reaction mixture was allowed to cool to ambient temperature. The solids were removed by filtration and washed with 14 mL of toluene. The combined filtrates were concentrated to dryness to afford crude liquid, the triester 5b. $^1$H NMR (400 MHz, CDCl$_3$) 4.21-4.03 (m, 8H), 3.62-3.34 (m, 6H), 2.84-2.34 (m, 4H), 1.61-1.50 (m, 2H), 1.36-1.04 (m, 13H), 0.92-0.79 (m, 3H); LC-MS, m/z calcd for C$_{20}$H$_{36}$N$_2$O$_7$: 416.25. found (M+1)$^+$ 417.2.

Example 3

N-(2-Ethyl)-Hexanoyl-Ethylenediamine-N,N'N'-Triacetic Acid Ethyl Triester, 5c

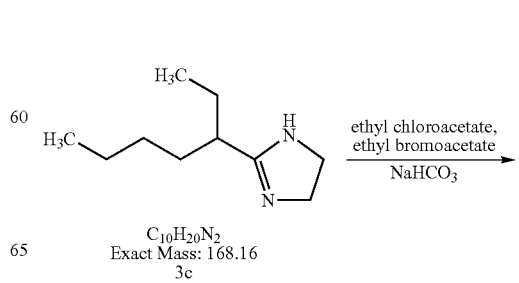

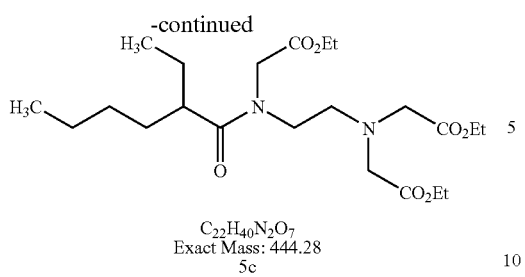

C$_{22}$H$_{40}$N$_2$O$_7$
Exact Mass: 444.28
5c

A 250 mL 3-necked flask was charged under nitrogen atmosphere with 50.4 mL of toluene, 16.8 g (0.10 mol) 2-(2'-ethylpentyl)-imidazoline, 3c, 33.6 g (0.4 mol) sodium bicarbonate, 28.8 mL (0.27 mol) ethyl chloroacetate, and 5.53 mL (0.05 mol) ethyl bromoacetate. The mixture was heated to 100° C. for 8 hrs and HPLC analysis indicated complete reaction. The reaction mixture was allowed to cool to ambient temperature. The solids were removed by filtration and washed with 16.8 mL of toluene. The combined filtrates were concentrated to dryness to afford crude liquid, the triester 5c. $^1$H NMR (400 MHz, CDCl$_3$) 4.14-3.98 (m, 8H), 3.55 (s, 2H), 3.50-3.37 (m, 2H), 3.34 (s, 4H), 2.81-2.37 (m, 1H), 1.55-1.25 (m, 4H), 1.23-1.15 (m, 13H), 0.91-0.77 (0.6H); LC-MS, m/z calcd for C$_{22}$H$_{40}$N$_2$O$_7$: 444.3. found (M+1)$^+$ 444.3.

Example 4

N-Lauroyl-Ethylenediamine-N,N'N'-Triacetic Acid Ethyl Triester, 5d

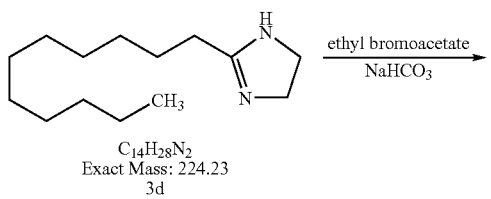

C$_{14}$H$_{28}$N$_2$
Exact Mass: 224.23
3d

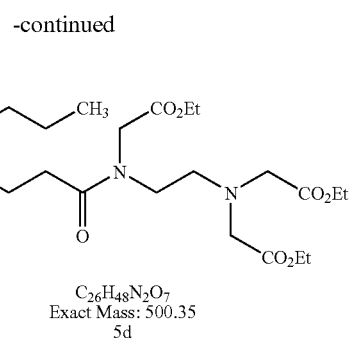

C$_{26}$H$_{48}$N$_2$O$_7$
Exact Mass: 500.35
5d

A 250 mL 3-necked flask was charged under nitrogen atmosphere with 44.8 mL of toluene, 22.4 g (0.10 mol) 2-undecylimidazoline, 3d, 42.0 g (0.5 mol) sodium bicarbonate and 38.7 mL (0.35 mol) ethyl bromoacetate. The mixture was heated to 100° C. for 8 hrs and HPLC analysis indicated complete reaction. The reaction mixture was allowed to cool to ambient temperature. The solids were removed by filtration and washed with 22.4 mL of toluene. The combined filtrates were concentrated to dryness to afford crude liquid, the triester 5d. $^1$H NMR (400 MHz, CDCl$_3$) 4.16-4.00 (m, 8H), 3.54 (s, 2H), 3.49-3.30 (m, 4H), 2.88-2.70 (m, 2H), 2.35-2.11 (m, 2H), 1.47-1.32 (m, 2H), 1.30-1.10 (m, 25H), 0.89-0.79 (m, 3H); LC-MS, m/z calcd for C$_{26}$H$_{48}$N$_2$O$_7$: 500.35. found (M+1)$^+$ 501.3.

Example 5

N-Hexanoyl-(Propane-1,2-diamine)-N,N'N'-Triacetic Acid Ethyl Triesters, 5ea and 5eb

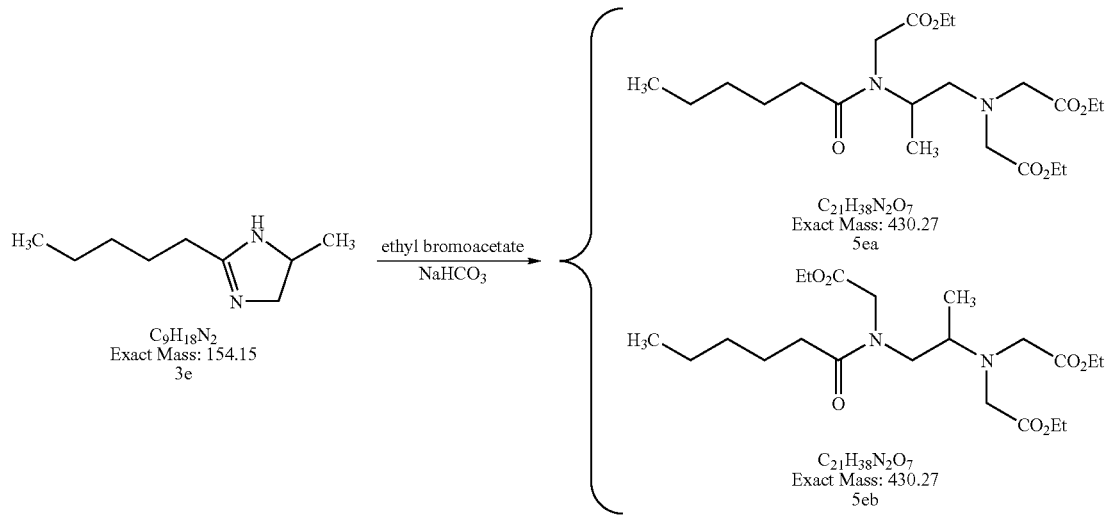

A 250 mL 3-necked flask was charged under nitrogen atmosphere with 70 ml of toluene, 35 g (0.23 mol) 5-methyl-2-pentyl-4,5-dihydro-1H-imidazole, 3e, 95.30 g (1.13 mol) sodium bicarbonate and 87.9 mL (0.79 mol) ethyl bromoacetate. The mixture was heated to 100° C. for 8 hrs and HPLC analysis indicated complete reaction. The reaction mixture was allowed to cool to ambient temperature. The solids were removed by filtration and washed with 35 mL of toluene. The combined filtrates were concentrated to dryness to afford crude liquid. After silica-gel chromatographic purification, two isomeric triesters were separated.

Compound 5ea: $^1$H NMR (400 MHz, d$_6$-DMSO) 4.59-445 (m, 1H), 4.43 (s, 2H); 4.00 (s, 2H); 3.98-3.62 (m, 8H), 3.33-3.29 (m, 2H), 2.31-2.15 (m, 2H), 1.37-1.31 (m, 2H), 1.16-0.88 (m, 16), 0.78-0.66 (m, 3H); LC-MS, m/z calcd for $C_{21}H_{38}N_2O_7$: 430.27. found (M+1)$^+$ 431.2.

Compound 5eb: $^1$H NMR (400 MHz, d$_6$-DMSO) 4.77-4.72 (m, 1H); 4.41-3.94 (m, 2H), 3.67-3.61 (m, 1H), 3.22-3.15 (m, 1H), 2.50-2.20 (m, 2H), 1.75-1.45 (m, 2H), 1.38-1.08 (m, 16), 0.91-0.78 (m, 3H); LC-MS, m/z calcd for $C_{21}H_{38}N_2O_7$: 430.27. found (M+1)$^+$ 431.2.

Example 6

N-Nonanoyl-Ethylenediamine-N,N',N'-Triacetic Acid, 6a

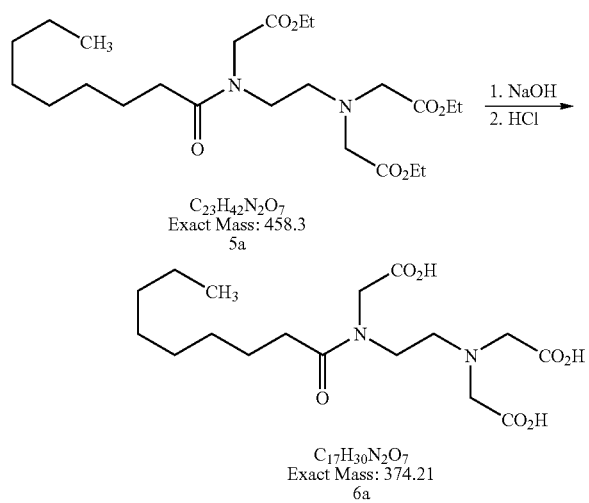

A 1.0 L 3-necked round bottom flask equipped with a thermocouple, a pH probe, and overhead stirrer was charged with 251 g (0.522 mol) triester 5a, and 25 mL methanol. To the stirring solution was added 287 mL of 6N NaOH under controlled conditions; pH was maintained around 12±1. The reaction mixture was stirred at room temperature for 2 hrs. It was then acidified with 315 mL of 6N HCl to pH=2.0. The formed light brown suspension was filtered, washed with 500 mL water, and 250 mL acetone. The wet cake was triturated with 500 mL isopropanol at 40° C. for 2 hrs. After cooling to room temperature, the white solids were filtered, washed with 250 mL of acetone, and dried in a vacuum oven at 45° C. to afford 152.5 g (78% yield) of 6a as a white solid. $^1$H NMR (400 MHz, d$_6$-DMSO) 12.38 (b, 3H), 4.16-3.94 (d, 2H), 3.55-3.30 (m, 6H), 2.80-2.70 (dt, 2H), 2.35-2.11 (dt, 2H), 1.46-1.45 (m, 2H), 1.25-1.23 (0.10H), −0.87-0.84 (t, 3H); LC-MS, m/z calcd for $C_{17}H_{30}N_2O_7$: 374.2. found (M+1)$^+$ 475.2.

Example 7

N-Hexanoyl-Ethylenediamine-N,N',N'-Triacetic Acid, 6b

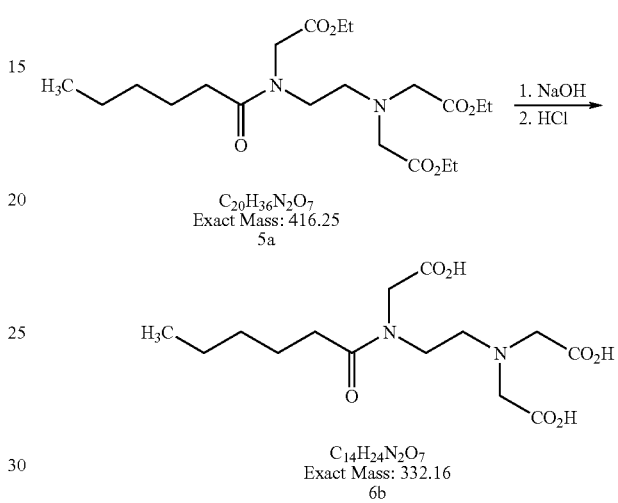

A 100 ml 3-necked round bottom flask equipped with a thermocouple, a pH probe, and overhead stirrer was charged with 6.69 g (16.1 mmol) triester 5b and 0.67 mL methanol. To the stirring solution was added 8.03 mL of 6N NaOH under controlled conditions; pH was maintained around 12±1. The reaction mixture was stirred at room temperature for 2 hrs. It was then acidified with 8.30 mL of 6N HCl to pH=2.0. The mixture was extracted with 3×15 mL ethyl acetate. The aqueous layer was concentrated to dryness to obtain pale yellow solid 6b. $^1$H NMR (400 MHz, d$_6$-DMSO) 12.38 (b, 3H), 4.03-3.86 (d, 2H), 3.83-3.54 (m, 6H), 2.44-2.29 (dt, 2H), 2.35-2.11 (dt, 2H), 1.54-1.42 (m, 2H), 1.28-1.28 (m, 4H), 0.84 (t, 3H); LC-MS, m/z calcd for $C_{14}H_{24}N_2O_7$: 332.16. found (M+1)$^+$ 332.

Example 8

N-(2-Ethyl-Hexanoyl)-Ethylenediamine-N,N',N'-Triacetic Acid, 6c

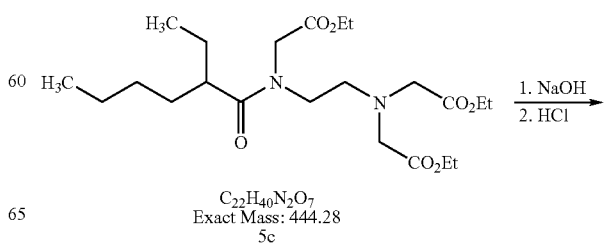

-continued

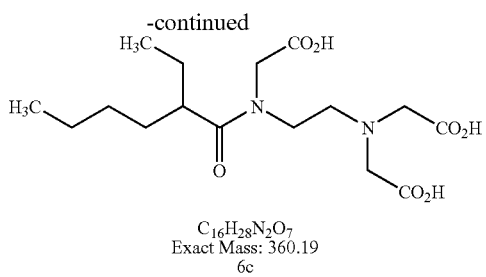

C$_{16}$H$_{28}$N$_2$O$_7$
Exact Mass: 360.19
6c

A 100 mL 3-necked round bottom flask equipped with a thermocouple, a pH probe, and overhead stirrer was charged with 2.92 g (6.57 mmol) triethylester 5c and 0.29 mL methanol. To the stirring solution was added 3.28 mL of 6N NaOH under controlled conditions; pH was maintained around 12±1. The reaction mixture was stirred at room temperature for 2 hrs. It was then acidified with 3.39 mL of 6N HCl to pH=2.0. The solution was extracted with 10 mL ethyl acetate three times. The combined organic layers were washed with 20 mL brine, dried over sodium sulfate and concentrated to dryness to obtain pale yellow solid 6c. $^1$H NMR (400 MHz, d$_6$-DMSO) 12.46 (b, 3H), 4.33-3.3.55 (m, 8H), 3.49-3.77 (m, 3H), 2.90-2.37 (m, 2H), 1.48-1.6 (m, 4H), 1.05-1.03 (m, 2H), 0.85-0.76 (m, 6H); LC-MS, m/z calcd for C$_{16}$H$_{28}$N$_2$O$_7$: 360.19. found (M+1)$^+$ 361.

Example 9

N-Lauroyl-Ethylenediamine-N,N'N'-Triacetic Acid, 6d

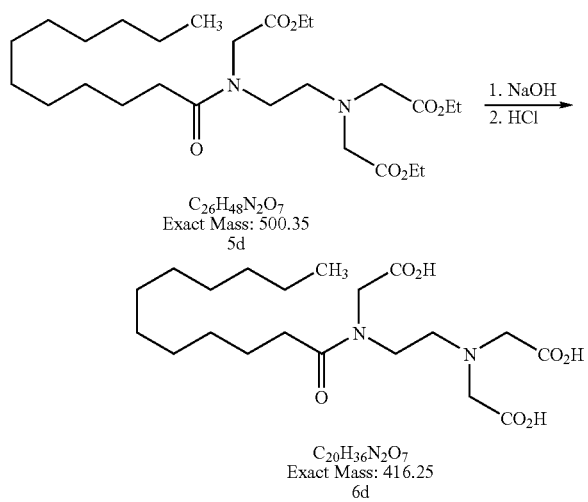

A 100 mL 3-necked round bottom flask equipped with a thermocouple, a pH probe, and overhead stirrer was charged with 9.72 g (19.4 mmol) triester 5d and 0.97 mL methanol. To the stirring solution was added 9.70 mL of 6N NaOH under controlled conditions; pH was maintained around 12±1. The reaction mixture was stirred at room temperature for 2 hrs. It was then acidified with 10.03 mL of 6N HCl to pH=2.0. The mixture was allowed to crystallize and the light brown solids were filtered, washed with 19.5 mL water, and 9.72 mL acetone. The wet cake was triturate with 19.5 mL isopropanol at 40° C. for 2 hrs. After cooling to room temperature, the solids were filtered, washed with 9.72 mL of acetone, and dried in a vacuum oven at 45° C. to afford 6d as an off-white solid. $^1$H NMR (400 MHz, d$_6$-DMSO) 12.40 (b, 3H), 4.16-3.3.94 (d, 2H), 3.54-3.31 (m, 6H), 2.81-2.73 (m, 2H), 2.35-231 (m, 2H), 1.46-1.44 (m, 2H), 1.25 (m, 16H), 0.88-0.84 (t, 3H); LC-MS, m/z calcd for C$_{20}$H$_{36}$N$_2$O$_7$: 416.25. found (M+1)$^+$ 417.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of preparing a compound of Formula (I):

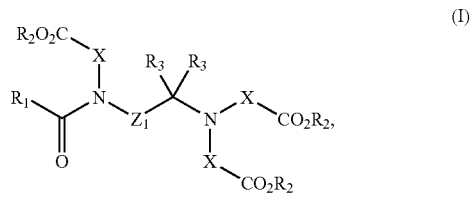

wherein:

Z$_1$ can be present or absent and when present is —[C(R$_4$)$_2$]$_m$—;

m is an integer from 1 to 4;

each X is —CHR$_5$—[C(R$_6$)$_2$]$_n$—;

each n is independently an integer from 0 to 4;

R$_1$ is selected from the group consisting of H, alkyl, cycloalkyl, substituted alkyl, aralkyl, aryl, and substituted aryl;

each R$_2$ is independently selected from the group consisting of alkyl, cycloalkyl, substituted alkyl, aralkyl, aryl, and substituted aryl;

each R$_3$ and each R$_4$ are independently selected from the group consisting of H, alkyl, cycloalkyl, substituted alkyl, aralkyl, aryl, and substituted aryl, or wherein one R$_3$ and one R$_4$ are together alkylene, substituted alkylene, aralkylene, or substituted aralkylene, or wherein two R$_4$ are together alkylene, substituted alkylene, aralkylene, or substituted aralkylene;

each R$_5$ is selected from the group consisting of H, alkyl, cycloalkyl, substituted alkyl, aralkyl, aryl, and substituted aryl; and each R$_6$ is independently selected from the group consisting of H, alkyl, alkoxy, cycloalkyl, aralkyl, aralkoxy, aryloxy, aryl, and substituted aryl; wherein the method comprises:

providing a cyclic amidine compound, wherein the cyclic amidine compound is a cyclic amidine wherein the amidine nitrogen atoms are linked via an alkylene or aralkylene group; and contacting the cyclic amidine compound with an ester of a haloalkanoic acid in the presence of a base.

2. The method of claim 1, wherein R$_1$ is selected from the group consisting of alkyl, cycloalkyl, substituted alkyl, aralkyl, aryl, and substituted aryl, and wherein the cyclic amidine is a compound of Formula (II):

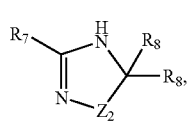
(II)

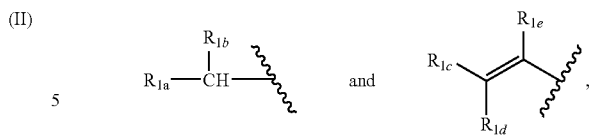
and, wherein:
- $Z_2$ can be present or absent and when present is $-[C(R_9)_2]_m-$;
- m is an integer from 1 to 4;
- $R_7$ is selected from the group consisting of alkyl, cycloalkyl, substituted alkyl, aralkyl, aryl and substituted aryl; and
- each $R_8$ and each $R_9$ are independently selected from the group consisting of H, alkyl, cycloalkyl, substituted alkyl, aralkyl, aryl and substituted aryl, or wherein one $R_8$ and one $R_9$ together are alkylene, substituted alkylene, aralkylene, or substituted aralkylene, or wherein two $R_9$ together are alkylene, substituted alkylene, aralkylene, or substituted aralkylene.

3. The method of claim 1, wherein the cyclic amidine is a 2-substituted imidazoline.

4. The method of claim 3, wherein the compound of Formula (I) has a structure of Formula (Ia):

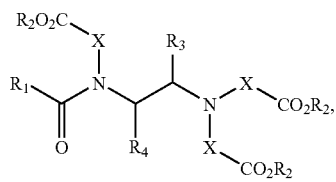
(Ia)

wherein:
- each X is $-CHR_5-[C(R_6)_2]_n-$;
- each n is independently an integer from 0 to 4;
- $R_1$ is selected from the group consisting of alkyl, cycloalkyl, substituted alkyl, aralkyl, aryl, and substituted aryl;
- each $R_2$ is independently selected from the group consisting of alkyl, cycloalkyl, substituted alkyl, aralkyl, aryl, and substituted aryl;
- $R_3$ and $R_4$ are independently selected from the group consisting of H, alkyl, cycloalkyl, substituted alkyl, aralkyl, aryl, and substituted aryl, or wherein $R_3$ and $R_4$ together are alkylene, substituted alkylene, aralkylene, or substituted aralkylene;
- each $R_5$ is selected from the group consisting of H, alkyl, cycloalkyl, substituted alkyl, aralkyl, aryl, and substituted aryl; and
- each $R_6$ is independently selected from the group consisting of H, alkyl, alkoxy, cycloalkyl, aralkyl, aralkoxy, aryloxy, aryl, and substituted aryl.

5. The method of claim 4, wherein each n is 0.

6. The method of claim 4, wherein $R_1$ is alkyl.

7. The method of claim 6, wherein the alkyl is straight-chain, saturated alkyl.

8. The method of claim 6, wherein the alkyl is C1-C12 alkyl.

9. The method of claim 8, wherein the alkyl is C8 alkyl.

10. The method of claim 4, wherein $R_1$ has a structure of one of the formulas:

wherein $R_{1a}$ and $R_{1b}$ are independently selected from the group consisting of alkyl, substituted alkyl, cycloalkyl, aralkyl, aryl, and substituted alkyl, and wherein $R_{1c}$, $R_{1d}$ and $R_{1e}$ are independently selected from the group consisting of H, alkyl, substituted alkyl, cycloalkyl, aralkyl, aryl, and substituted alkyl.

11. The method of claim 4, wherein each $R_2$ is C1-C6 alkyl.

12. The method of claim 11, wherein each $R_2$ is ethyl.

13. The method of claim 4, wherein $R_3$ and $R_4$ are independently selected from H and alkyl.

14. The method of claim 4, wherein each $R_5$ is selected from the group consisting of H and alkyl.

15. The method of claim 4, wherein the 2-substituted imidazoline is a compound of Formula (IIa):

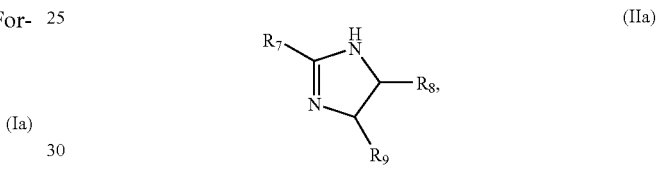
(IIa)

wherein:
- $R_7$ is selected from the group consisting of alkyl, cycloalkyl, substituted alkyl, aralkyl, aryl and substituted aryl; and
- $R_8$ and $R_9$ are independently selected from the group consisting of H, alkyl, cycloalkyl, substituted alkyl, aralkyl, aryl and substituted aryl, or wherein $R_8$ and $R_9$ together are alkylene, substituted alkylene, aralkylene, or substituted aralkylene.

16. The method of claim 15, wherein $R_7$ is saturated alkyl.

17. The method of claim 15, wherein $R_7$ is C1-C12 alkyl.

18. The method of claim 15, wherein one or both of $R_8$ and $R_9$ is H.

19. The method of claim 15, wherein one or both of $R_8$ and $R_9$ is alkyl.

20. The method of claim 19, wherein one or both of $R_8$ and $R_9$ is methyl.

21. The method of claim 1, wherein the ester is the ester of an α-haloacetic acid or a mixture thereof.

22. The method of claim 21, wherein the ester is ethyl chloroacetate, ethyl bromoacetate, or a mixture thereof.

23. The method of claim 1, wherein the contacting is performed in an aprotic, non-polar solvent.

24. The method of claim 23, wherein the aprotic, non-polar solvent is toluene.

25. The method of claim 1, wherein the base is sodium bicarbonate.

26. A method for preparing a N-acyl-N,N',N'-alkylenediamine trialkanoic acid or a salt thereof, wherein the method comprises:
providing a cyclic amidine compound, wherein the cyclic amidine compound is a cyclic amidine wherein the amidine nitrogen atoms are linked via an alkylene or aralkylene group;

contacting the cyclic amidine compound with an ester of a haloalkanoic acid in the presence of a first base to provide a compound of Formula (I):

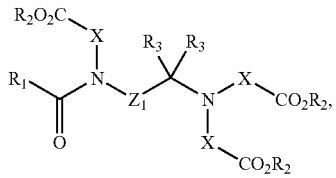

wherein:
$Z_1$ can be present or absent and when present is $-[C(R_4)_2]_m-$;
m is an integer from 1 to 4;
each X is $-CHR_5-[C(R_6)_2]_n-$;
each n is independently an integer from 0 to 4;
$R_1$ is selected from the group consisting of H, alkyl, cycloalkyl, substituted alkyl, aralkyl, aryl, and substituted aryl;
each $R_2$ is independently selected from the group consisting of alkyl, cycloalkyl, substituted alkyl, aralkyl, aryl, and substituted aryl;
each $R_3$ and each $R_4$ are independently selected from the group consisting of H, alkyl, cycloalkyl, substituted alkyl, aralkyl, aryl, and substituted aryl, or wherein one $R_3$ and one $R_4$ together alkylene, substituted alkylene, aralkylene, or substituted aralkylene, or wherein two $R_4$ are together alkylene, substituted alkylene, aralkylene, or substituted aralkylene;
each $R_5$ is selected from the group consisting of H, alkyl, cycloalkyl, substituted alkyl, aralkyl, aryl, and substituted aryl; and
each $R_6$ is independently selected from the group consisting of H, alkyl, alkoxy, cycloalkyl, aralkyl, aralkoxy, aryloxy, aryl, and substituted aryl; and
contacting the compound of Formula (I) with a second base.

27. The method of claim 26, wherein the N-acyl-N,N',N'-alkylenediamine trialkanoic acid or salt thereof is a N-acyl-N,N',N'-ethylenediamine trialkanoic acid or a salt thereof, and wherein:
providing the cyclic amidine compound comprises providing a 2-substituted imidazoline;
contacting the cyclic amidine compound with the ester of a haloalkanoic acid in the presence of the first base to provide the compound of Formula (I) comprises contacting the 2-substituted imidazoline with the ester of a haloalkanoic acid in the presence of the first base to provide a compound of Formula (I) wherein the compound of Formula (I) is a compound of Formula (Ia):

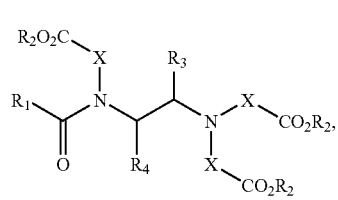

wherein:
each X is $-CHR_5-[C(R_6)_2]_n-$;
each n is independently an integer from 0 to 4;
$R_1$ is selected from the group consisting of alkyl, cycloalkyl, substituted alkyl, aralkyl, aryl, and substituted aryl;
each $R_2$ is independently selected from the group consisting of alkyl, cycloalkyl, substituted alkyl, aralkyl, aryl, and substituted aryl;
$R_3$ and $R_4$ are independently selected from the group consisting of H, alkyl, cycloalkyl, substituted alkyl, aralkyl, aryl, and substituted aryl, or wherein $R_3$ and $R_4$ together are alkylene, substituted alkylene, aralkylene, or substituted aralkylene;
each $R_5$ is independently selected from the group consisting of H, alkyl, cycloalkyl, substituted alkyl, aralkyl, aryl, and substituted aryl; and
each $R_6$ is independently selected from the group consisting of H, alkyl, alkoxy, cycloalkyl, aralkyl, aralkoxy, aryloxy, aryl, and substituted aryl; and
contacting the compound of Formula (I) with the second base comprises contacting the compound of Formula (Ia) with the second base.

28. The method of claim 26, wherein the second base is an alkali metal hydroxide.

29. The method of claim 26, wherein contacting the compound of Formula (I) with the second base comprises providing a mixture comprising the compound of Formula (I) and the second base; mixing the mixture for a period of time; and acidifying the mixture with an acid.

* * * * *